(12) United States Patent
Yamamoto et al.

(10) Patent No.: US 7,613,502 B2
(45) Date of Patent: Nov. 3, 2009

(54) OPTICAL BIOINSTRUMENTATION FOR LIVING BODY

(75) Inventors: Yukari Yamamoto, Kunitachi (JP); Atsushi Maki, Fuchu (JP); Masashi Kiguchi, Kawagoe (JP); Tsuyoshi Yamamoto, Matsudo (JP)

(73) Assignee: Hitachi, Ltd., Tokyo (JP)

( * ) Notice: Subject to any disclaimer, the term of this patent is extended or adjusted under 35 U.S.C. 154(b) by 686 days.

(21) Appl. No.: 11/205,184

(22) Filed: Aug. 17, 2005

(65) Prior Publication Data

US 2006/0100526 A1    May 11, 2006

(30) Foreign Application Priority Data

Oct. 26, 2004   (JP)   ............... 2004-310696

(51) Int. Cl.
    *A61B 5/00*   (2006.01)
(52) U.S. Cl. .................................... 600/473
(58) Field of Classification Search ........... 600/310, 600/476, 473, 344, 429, 407, 409, 334; 348/51; 356/41
    See application file for complete search history.

(56) References Cited

U.S. PATENT DOCUMENTS

| | | | | | |
|---|---|---|---|---|---|
| 5,103,805 | A | * | 4/1992 | Okazaki | 601/4 |
| 5,662,111 | A | * | 9/1997 | Cosman | 600/417 |
| 6,167,292 | A | * | 12/2000 | Badano et al. | 600/407 |
| 6,282,438 | B1 | * | 8/2001 | Maki et al. | 600/476 |
| 6,542,763 | B1 | * | 4/2003 | Yamashita et al. | 600/310 |
| 6,611,283 | B1 | * | 8/2003 | Isonuma | 348/51 |
| 2001/0027272 | A1 | * | 10/2001 | Saito et al. | 600/426 |
| 2003/0004392 | A1 | | 1/2003 | Tanner et al. | |
| 2003/0088162 | A1 | * | 5/2003 | Yamamoto et al. | 600/310 |

FOREIGN PATENT DOCUMENTS

| | | |
|---|---|---|
| EP | 1323380 | 7/2003 |
| JP | 2001-198112 | 7/2001 |
| JP | 2004-194701 | 7/2004 |

OTHER PUBLICATIONS

Spatial and Temporal Analysis of Human Motor Activity Using Noninvasive NIR Topography, Maki et al. pp. 1997-2005, Med. Phys. 22 (12), Dec. 1995.
Arranging Optical Fibres for the Spatial Resolution Improvement of Topograchical Images, Yamamoto et al., 3429-3440., Phys. Med. Biol. 47 (2002).

* cited by examiner

*Primary Examiner*—Eric F Winakur
*Assistant Examiner*—Lawrence N Laryea
(74) *Attorney, Agent, or Firm*—Brundidge & Stanger, P.C.

(57) ABSTRACT

In a probe positioning technology, an optical bioinstrumentation includes a region selecting unit that is used to delineate a region of interest in an anatomical image of a subject, a computing unit that determines a recommended probe position according to the region of interest, a probe position sensor that detects a current probe position, a computing unit that calculates the distance between the recommended probe position and the current probe position, and an alarm device that generates an alarm sound or the like when the distance falls within a predetermined range. Moreover, the optical bioinstrumentation for living body further includes a memory unit in which the probe position is saved together with measurement data.

18 Claims, 15 Drawing Sheets

FIG.6
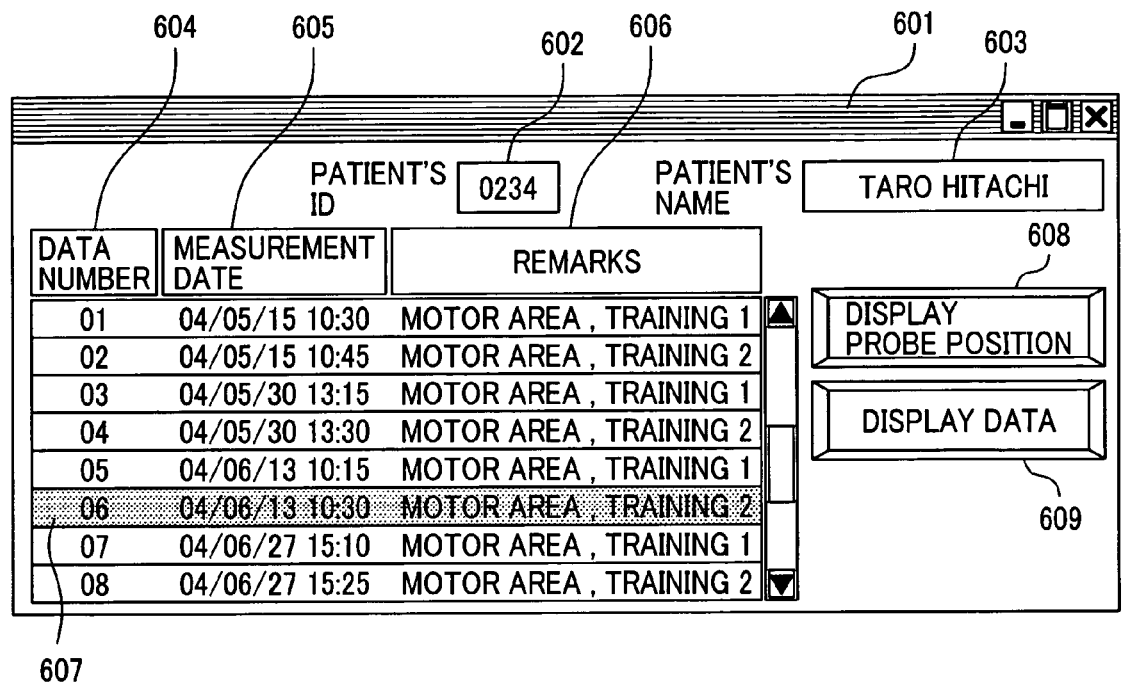
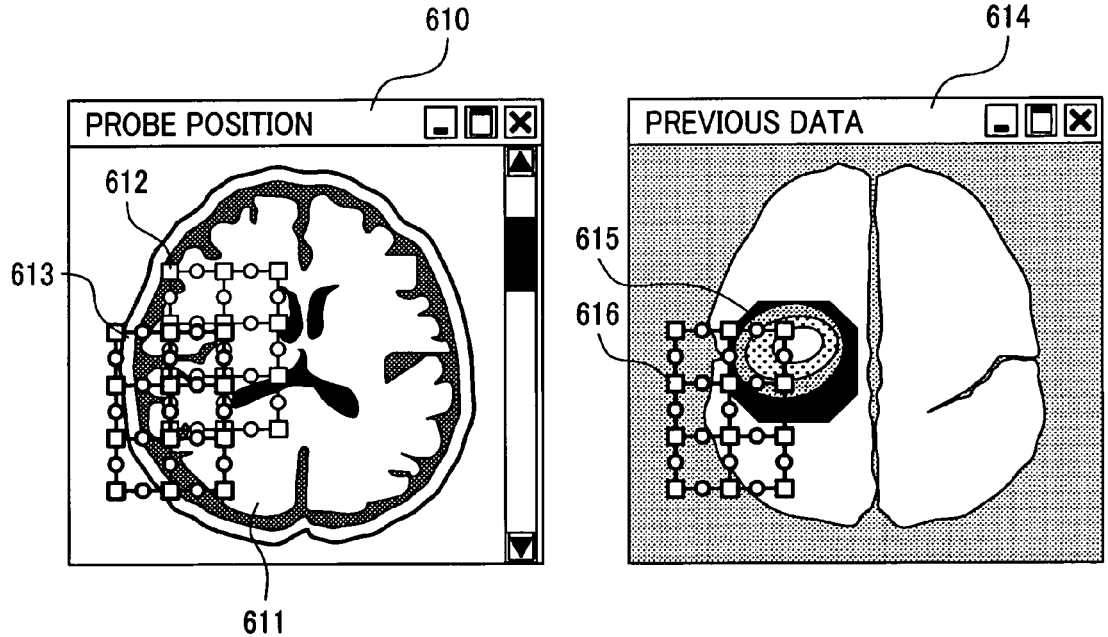

OPTICAL BIOINSTRUMENTATION FOR LIVING BODY

CLAIM OF PRIORITY

The present invention claims priority from Japanese application JP2004-310696 filed on Oct. 26, 2004, the content of which is hereby incorporated by reference on to this application.

BACKGROUND OF THE INVENTION

The present invention relates to the technology for biomeasurement using light that uses light to acquire intracorporeal information. More particularly, the present invention is concerned with the technology for biomeasurement using light that makes it possible to dispose a probe at a position at which high sensitivity is exhibited so as to thus improve positional reproducibility to be ensured at the time of remounting the probe.

Optical bioinstrumentations for living body are such that a light incidence/light detection probe is mounted on a region to be measured in order to acquire intracorporeal information. For example, a technology of acquiring spatiotemporal information on brain activities using near-infrared light with a plurality of light incidence/light detection probes mounted on a subject's head (refer to, for example, Non-Patent Document 1: "Medical Physics" written by A. Maki et al. (vol. 22, pp. 1997-2005, 1995). According to the technology, the near-infrared light incident on the scalp is detected at a distance of about 3 cm in order to measure a change in the concentration of hemoglobin in the cerebral cortex interposed between the incident point and the detection point. Since the local hemodynamics, that is, the concentration of hemoglobin varies depending on a brain activity, the spatiotemporal change of brain activities can be grasped. What counts in the measurement of brain activities is to learn in what cerebral region an activity takes place.

However, since the optical bioinstrumentation for living body cannot acquire anatomical information, an active region must be detected based on positional information acquired using other technique. Hereinafter, an image to be used to observe the shape or structure of the brain is called an anatomical image, and an image used to observe the state of brain activities by analyzing cerebral blood flows or any other information is called a brain functional image. As a modality for constructing the anatomical image, magnetic resonance imaging (MRI) or X-ray computed tomography (CT) may be adopted. Moreover, as a modality for constructing the brain functional image, in addition to the optical bioinstrumentation for living body, functional MRI (fMRI), positron emission tomography (PET), electroencephalography (EEG), magnetoencephalography (MEG), or single photon emission computed tomography (SPECT) may be adopted.

In a conventional optical bioinstrumentation for living body, a method for displaying an image, which expresses brain activities and is constructed by the optical bioinstrumentation for living body, while superimposing the image on a three-dimensional anatomical image constructed through MRI or X-ray CT has been proposed (refer to, for example, Patent Document 1: Japanese Patent Application Laid-Open No. 2001-198112). In order to construct the three-dimensional anatomical image, a reference point mark is drawn at a specific point on a subject. A three-dimensional position sensor such as a magnetometric sensor is used to measure coordinate values representing the position of the light incidence/light detection probe. The image expressing brain activities is positionally associated with the three-dimensional anatomical image using the position of the reference point mark as a reference.

As a technology making it possible to improve positional reproducibility to be ensured at the time of remounting a probe, a head gear for biomeasurement using light which includes a means for measuring a relative distance from an external marker of a subject has been proposed (refer to, for example, Patent Document 2: Japanese Patent Application Laid-Open No. 2004-194701). A measure that reads the relative distance between external markers is included in the shell of the head gear, and a light incidence/light detection probe is positioned according to the reading of the measure. In the technology, the probe can be easily positioned without the necessity of an anatomical image constructed by other modality.

The optical bioinstrumentation for living body detects near-infrared light, which is irradiated through an incident point on the scalp, at a detection point located at a distance of approximately 3 cm. Herein, a midpoint between the incident point and detection point is regarded as a sampling point. Moreover, a topographic image constructed based on measurement signals acquired from a plurality of sampling points is used to display the spatial distribution of brain activities. An experiment performed using a phantom has demonstrated that sensitivity expressed in the topographic image varies depending on a difference in the positional relationship between the sampling point and an activated area in the brain (refer to, for example, Non-Patent Document 2: "Physics in Medicine and Biology" written by T. Yamamoto et al. (vol. 47, pp. 3429-3440, 2002).

SUMMARY OF THE INVENTION

According to the optical bioinstrumentation for living body of the related art (Non-Patent Document 2), when an activated area in the brain is located immediately below a sampling point, immediately below an incident point or a detection point, or in the center of a square defined with two incident points and two detection points, if the activated area in the brain has a diameter of 10 mm, the detection sensitivity exhibited by the optical bioinstrumentation is 0.47, 0.28, or 0.28. Likewise, if the activated area in the brain has a diameter of 20 mm, the detection sensitivity is 0.70, 0.52, or 0.53.

Consequently, for higher-sensitivity measurement, a probe must be mounted so that a region to be measured will be located immediately below a sampling point to the greatest possible extent.

In general, what part of the brain is activated is left unknown until brain functional imaging is completed. If the results of experiments performed on a certain specific area under different conditions are compared with one another, or if the time-sequential change of brain activities is monitored, a region to be measured is determined in advance. For example, assuming that the effect of recovery of brain function of a stroke patient is monitored, a signal of brain-activity acquired from a certain area is observed. The change in the brain-activity signal is then analyzed in order to assess the effect of rehabilitation. In this case, compared with the strength of a signal acquired through normal biomeasurement using light, the signal strength is thought to be quite feeble. Therefore, measurement should preferably be performed in a state in which an optical bioinstrumentation for living body exhibits high sensitivity.

Moreover, when a change in a signal produced by an optical bioinstrumentation for living body is analyzed in order to assess the effect of rehabilitation for recovering the brain functions, a measurement error derived from a sensitivity distribution should preferably be minimized by improving the reproducibility of a position at which a probe is previously mounted:

As far as the optical bioinstrumentation for living body of the related art (Patent Document 1) is concerned, a positional relationship between a measurement area and an anatomical image can be checked after measurement is completed. However, no consideration is taken into whether the positional relationship between a sampling point and an activated area can be grasped in the stage of measurement. A probe cannot therefore always be mounted at a position at which the optical bioinstrumentation for living body exhibits high sensitivity. The reproducibility of a position at which the probe is previously mounted, that is, whether a position at which the probe is previously mounted can be reproduced at the time of remounting the probe is not taken into account.

Moreover, in the optical bioinstrumentation for living body of the related art (Patent Document 2), the inclusion of a measure in a shell helps improve the reproducibility of a position, at which a probe is previously mounted, to be ensured at the time of re-measurement. However, since there is difficulty in inferring the internal structure of the brain from the external side of the head, the probe cannot always be mounted at a position at which maximum sensitivity is exhibited.

Accordingly, an object of the present invention is to provide a technology for biomeasurement using light which ensures high positional reproducibility at the time of remounting a probe by disposing an optical irradiator and an optical detector at a position at which maximum sensitivity is exhibited.

For accomplishment of the object of the present invention, a bioinstrumentation for living body in accordance with the present invention has features described below.

(1) The bioinstrumentation for living body comprises: a probe that includes a means of irradiation which irradiates light to a subject and a means of detection which detects transilluminated light which has been irradiated from the means of irradiation and has been propagated through the subject, and that is mounted on the subject; a computing unit that calculates a concentration of metabolite in the subject according to a signal detected by the means of detection; and a display unit that displays an indicator indicating the concentration of metabolite calculated by the computing unit. Herein, representations expressing the positions of the means of irradiation and the means of detection are displayed on the display unit while being superimposed on an anatomical image of the subject or a brain functional image thereof. A position on the subject at which the probe should be mounted is determined based on the superimposed display.

(2) In the optical bioinstrumentation for living body set forth in (1), a substantial midpoint between the means of irradiation and the means of detection is regarded as a sampling point. The representations expressing the positions on the subject of the means of irradiation and the means of detection and a representation expressing the position of the sampling point are displayed on the display unit while being superimposed on the anatomical image of the subject or the brain functional image thereof.

(3) The optical bioinstrumentation for living body set for in (1) further comprises a memory unit in which the anatomical image of the subject or the brain functional image thereof is saved. The representations expressing the positions on the subject of the means of irradiation a nd the means of detection are displayed on the display unit while being superimposed on the anatomical image or brain functional image that is constructed prior to measurement and saved in the memory unit.

(4) The optical bioinstrumentation for living body set forth in (1) further comprises a means for giving the alarm when the distance between a predetermined measurement area expressed by a representation contained in the anatomical image or brain functional image and the position of the sampling point falls within a predetermined range. Moreover, the means for giving the alarm is realized with an audio apparatus that generates an alarm sound, or a representation signifying that the alarm is given is displayed on the display unit.

(5) The optical bioinstrumentation for living body set forth in (1) further comprises a position sensor that detects a three-dimensional position of the probe. When the distance between a predetermined measurement area expressed by a representation contained in the anatomical image or brain functional image and the three-dimensional position of the probe falls within a predetermined range, the alarm is given.

(6) The optical bioinstrumentation for living body set forth in (1) further comprises a control unit that uses the position sensor to dispose the probe at a position on the subject corresponding to the predetermined measurement area expressed by a representation contained in the anatomical image or brain functional image.

(7) In the optical bioinstrumentation for living body set forth in (1), the anatomical image or brain functional image is a three-dimensional image. Moreover, the anatomical image is an MRI image of the subject or an X-ray CT image thereof, and the brain functional image is any of an fMRI image of the subject, a PET image thereof, an electroencephalogram thereof, a magnetoencephalogram thereof, an optical image for living body thereof, and a SPECT image thereof.

(8) An optical bioinstrumentation for living body comprises: a probe that includes a means of irradiation which irradiates light to a subject and a means of detection which detects transilluminated light having been irradiated from the means of irradiation and having been propagated through the subject, and that is mounted on the subject; a computing unit that calculates a concentration of metabolite in the subject; a display unit that displays an indicator indicating the concentration of metabolite calculated by the computing unit; and a memory unit in which measurement data is saved. Herein, representations exhibiting the positions of the means of irradiation and the means of detection are displayed on the display unit while being superimposed on an anatomical image of the subject or a brain functional image thereof. A position on the subject at which the probe should be disposed is determined based on the superimposed display.

(9) In the optical bioinstrumentation for living body set forth in (8), the representations expressing the positions on the subject of the means of irradiation and the means of detection and the representations expressing positions on the subject at which the means of irradiation and the means of detection are disposed at the time of previous measurement and which are stored in the memory unit are displayed on the display unit while being superimposed on the anatomical image of the subject or the brain functional image thereof. A position on the subject at which the probe should be disposed at the time of re-measurement is determined based on the superimposed display.

(10) In the optical bioinstrumentation for living body set forth in (8), a substantial midpoint between the means of irradiation and the means of detection is regarded as a sampling point. The representations expressing the positions on the subject of the means of irradiation and the means of detection and the representation indicating the position of the sampling point are displayed on the display unit while being superimposed on the anatomical image of the subject or the brain functional image thereof.

(11) The optical bioinstrumentation for living body set forth in (8) further comprises a means for giving the alarm when the distance between a predetermined measurement area expressed by a representation contained in the anatomical image or brain functional image and the position of the sampling point falls within a predetermined range.

(12) The optical bioinstrumentation for living body set forth in (8) further comprises a means for giving the alarm when the distance between the positions on the subject at which the means of irradiation and the means of detection are disposed at the time of previous measurement and the current positions of the means of irradiation and the means of detection falls within a predetermined range. Moreover, the means for giving the alarm is realized with an audio apparatus that generates an alarm sound, or a representation signifying that the alarm is given is displayed on the display unit.

(13) In the optical bioinstrumentation for living body set forth in (8), the anatomical image or brain functional image is a three-dimensional image. Moreover, the anatomical image is an MRI image of the subject or an X-ray CT image thereof, and the brain functional image is any of an fMRI image of the subject, a PET image thereof, an electroencephalogram thereof, a magnetoencephalogram thereof, an optical image for living body thereof, and a SPECT image thereof.

(14) An optical bioinstrumentation for living body comprises: a probe that includes a plurality of pieces of means of irradiation that irradiate light to a subject and a plurality of pieces of means of detection that detect transilluminated light having been irradiated from the means of irradiation and having been propagated through the subject, and that is mounted on the subject; a computing unit that calculates a concentration of metabolite in the subject according to a signal detected by the means of detection; a display unit that displays an indictor indicating the concentration of metabolite calculated by the computing unit; and a memory unit in which measurement data is saved. Herein, a substantial midpoint between the means of irradiation and the means of detection is regarded as a sampling point. The representations expressing the positions on the subject of the means of irradiation and the means of detection and the representations expressing the positions on the subject at which the means of irradiation and the means of detection are disposed at the time of previous measurement are displayed on the display unit while being superimposed on an anatomical image of the subject or a brain functional image thereof. When the distance between a predetermined measurement area expressed by a representation contained in the anatomical image or brain functional image and the position of the sampling point falls within a predetermined range, and/or when the distances between the positions on the subject at which the means of irradiation and the means of detection are disposed at the time of previous measurement and the current positions of the means of irradiation and the means of detection fall within the predetermined range, the alarm is given.

According to the present invention, there is provided an optical bioinstrumentation for living body that ensures high positional reproducibility at the time of remounting a probe by disposing an optical irradiator and an optical detector at a position at which the optical bioinstrumentation exhibits maximum sensitivity.

BRIEF DESCRIPTION OF THE DRAWINGS

FIG. 6 shows an example of a previous data referencing means included in both the first and second embodiments and used to retrieve a previous probe position or previous measurement data;

DESCRIPTION OF THE PREFERRED EMBODIMENTS

Figure 1:
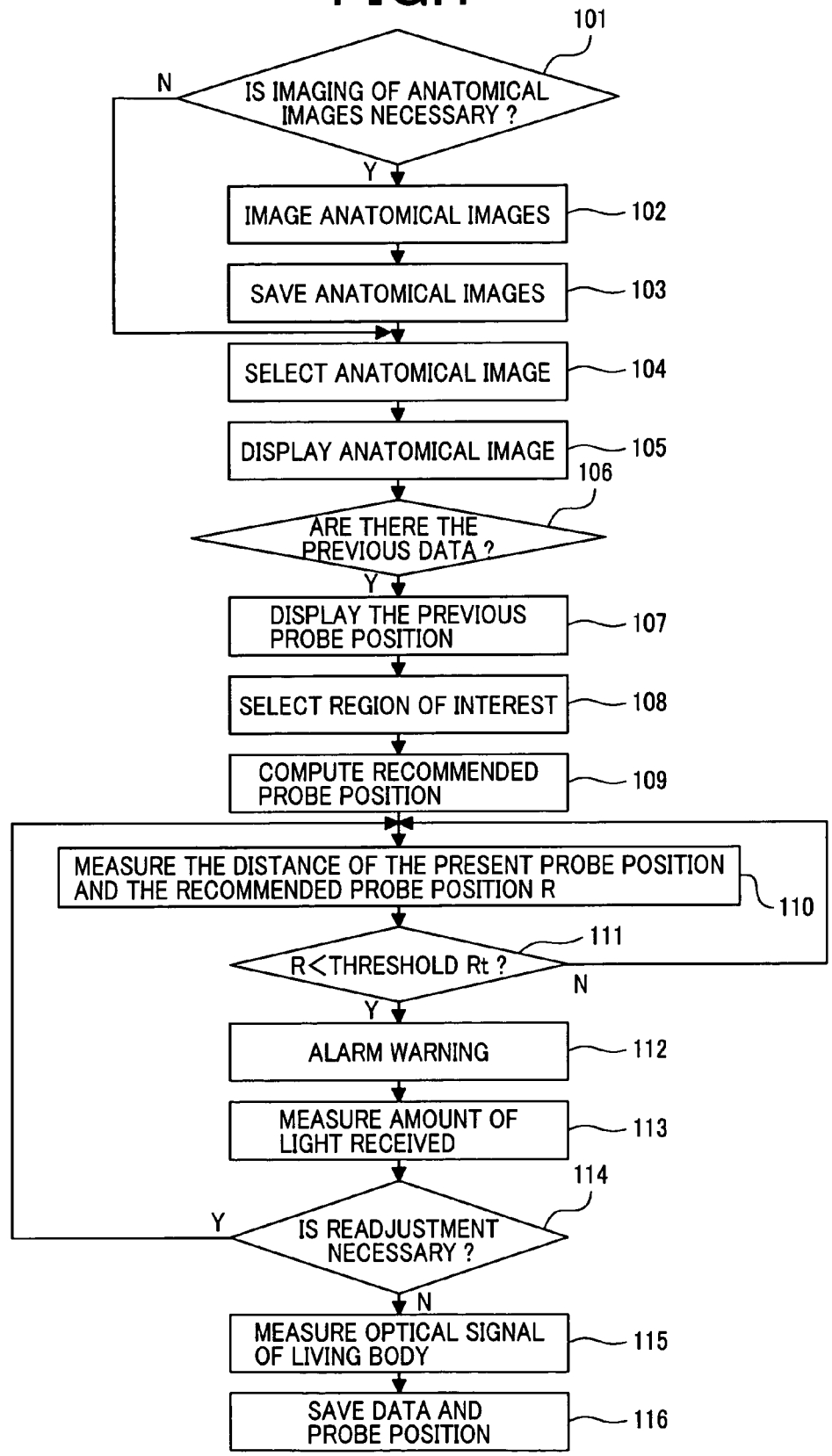
FIG. 1 is a flowchart describing a procedure of implementing the present invention.

Referring to the drawings, embodiments of the present invention will be described below.

First Embodiment

Figure 3:
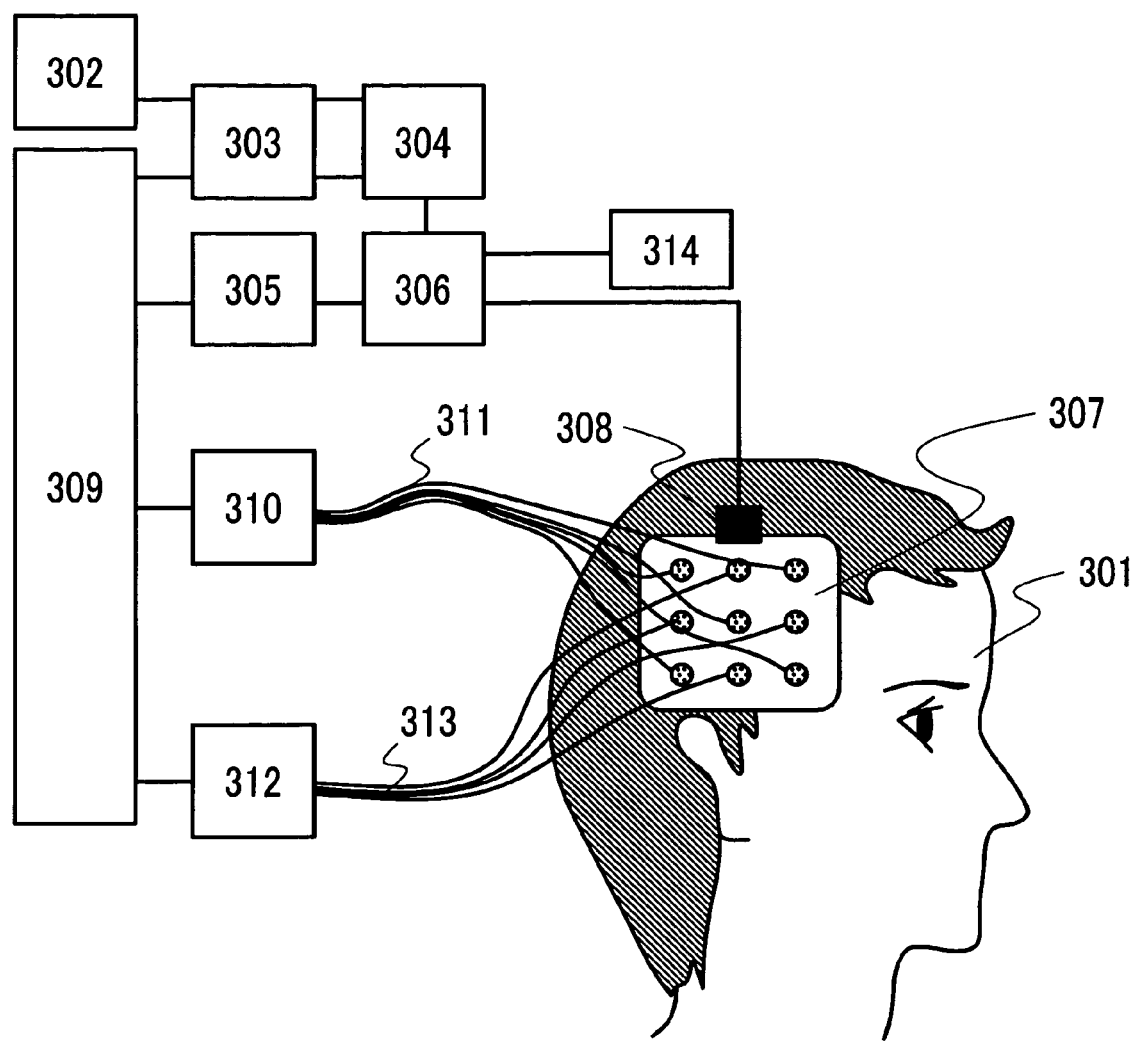
FIG. 3 is an explanatory image showing the configuration of the first embodiment.

FIG. 3 shows the configuration of an optical bioinstrumentation for living body in accordance with the first embodiment of the present invention.

An anatomical image of a subject 301 constructed in advance using an imager of anatomical image 302 is saved in a memory unit 303. An optical measurement and control unit 309 reads the anatomical image from the memory unit 303, and displays it on a display unit 304. A selecting region unit 305 designates a region of interest, and a computing unit 306 calculates a recommended probe position according to the region of interest. An optical fiber 311 is fixed to a probe 307 mounted on the head of the subject 301. Light irradiated from an optical irradiator 310 in response to an instruction sent from the optical measurement and control unit 309 is applied to the scalp of the subject 301 over the optical fiber 311. The light passing through the head of the subject 301 travels along an optical fiber 313 coupled to the probe 307, and is then detected by an optical detector 312. The computing unit 306 then performs signal processing. A probe position sensor 308 fixed to the probe 307 detects a three-dimensional position of the probe 307.

The computing unit 306 synthesizes the anatomical image saved in the memory unit 303, a representation expressing the recommended probe position, and a representation expressing the three-dimensional position of the probe 307 so as to construct a combined image, and displays the combined image on the display unit 304. Furthermore, when the distance between the recommended probe position and the three-dimensional position of the probe falls within a predetermined range of distances, the computing unit 306 causes an alarm device 314 to give the alarm.

The embodiment shown in FIG. 3 has been described on the assumption that an anatomical image of a subject constructed in advance and a representation of a probe position are synthesized to construct a combined image. Alternatively, a brain functional image expressing the subject's brain functions and being constructed in advance may be employed. The brain functional image is constructed using, for example, an fMRI system, a PET system, an electroencephalography system, a magnetoencephalography system, an optical bioinstrumentation for living body, or a SPECT system.

Figure 2:
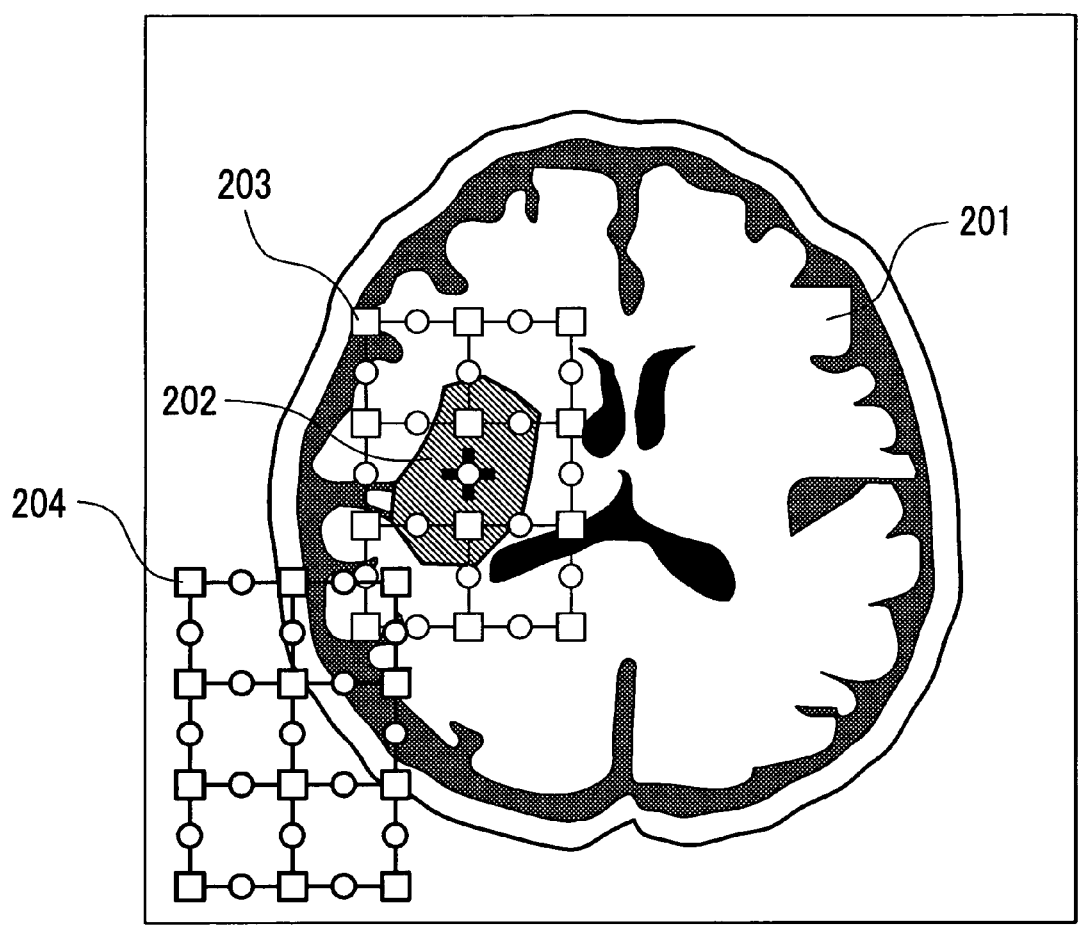
FIG. 2 shows an example of display attained when an anatomical image is displayed with representations expressing a region of interest, a recommended probe position, and a current probe position superimposed on the anatomical image according to the first or second embodiment.

FIG. 2 shows an example of display of the combined image. Referring to FIG. 2, there is shown an anatomical image 201 that is, for example, a three-dimensional image constructed by an MRI system or an X-ray CT system. Reference numeral 202 denotes a representation expressing a region of interest that is delineated in advance and that is, for example, an image which is sampled from the anatomical image and which expresses an infarcted area, a motor area, or any other specific area. Reference numeral 203 denotes a representation expressing a recommended probe position calculated from the position of the region of interest. Reference numeral 204 denotes a representation expressing a current probe position detected by the probe position sensor 308. The representation of the recommended probe position 203 and the representation of the current probe position 204 are displayed in different colors so that they can be discriminated from each other. Moreover, the representation of the region of interest 202 may be displayed while being superimposed on the anatomical image 201. In this case, for distinction of the position of the region of interest, the contour of the representation of the region of interest is displayed in a color different from the color of the anatomical image 201 and the colors of the representations of the recommended probe position 203 and current probe position 204, or displayed with their pixels set to a different pixel value. Moreover, an indicator expressing the center of gravity of the region of interest may be displayed while being superimposed on the anatomical image.

The embodiment shown in FIG. 2 has been described by taking for instance a case where representations expressing a region of interest and a probe position are displayed while being superimposed on an anatomical image. Alternatively, the representations expressing the region of interest and the probe position may be displayed while being superimposed on a brain functional image constructed by an fMRI system, a PET system, an electroencephalography system, a magnetoencephalography system, an optical bioinstrumentation for living body, or a SPECT system.

Figure 15:
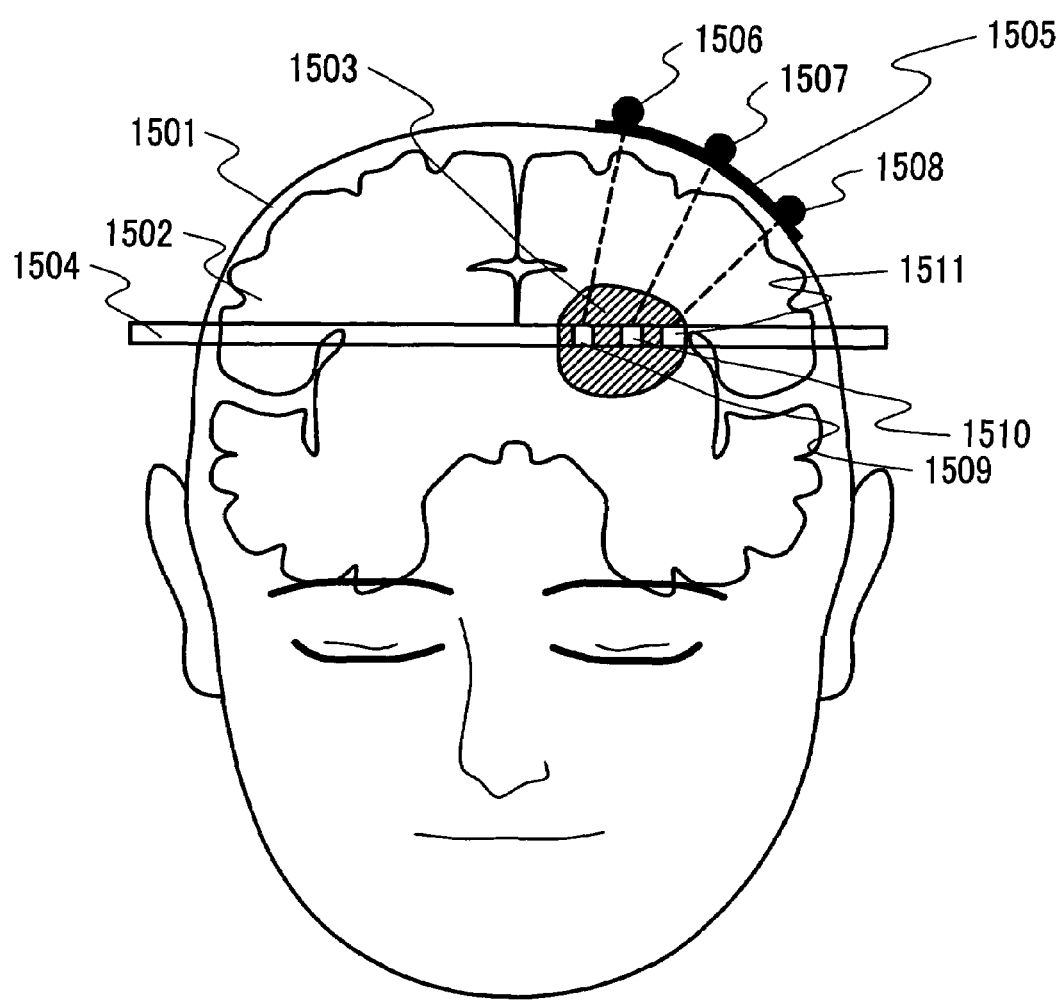
FIG. 15 is an explanatory diagram concerning a method of projecting a probe position onto a section expressed by an anatomical image according to the first or second embodiment.

Although a section expressed with an anatomical image is a plane, the scalp to which the probe 307 is fixed has a curved surface. Therefore, when a representation expressing a probe position is displayed while being superimposed on the anatomical image, the image of the section on which a probe position is projected as shown in FIG. 15 must be displayed. For example, assume that a section parallel to a section A (1504) containing an infarcted area 1503 in the brain 1502 is regarded as a section to be expressed with an anatomical image. When a probe 1505 is fixed at an illustrated position along the shape of the head, light irradiation (detection) fiber holders 1506 to 1508 equidistantly arranged on the probe are projected onto the section A (1504) to form positions 1509 to 1511. The positions 1509 to 1511 are positions at which normals to the positions 1506 to 1508 on the curved surface extending along the scalp 1501 intersects the section A (1504).

As shown in FIG. 15, according to the present embodiment, when it says that a representation of a probe position is displayed while being superimposed on an anatomical image, it means that a representation expressing a position formed by projecting the probe position is displayed while being superimposed on an anatomical image. The same applies to a case where a representation of a probe position is displayed while being superimposed on a brain functional image constructed through fMRI.

Figure 8:
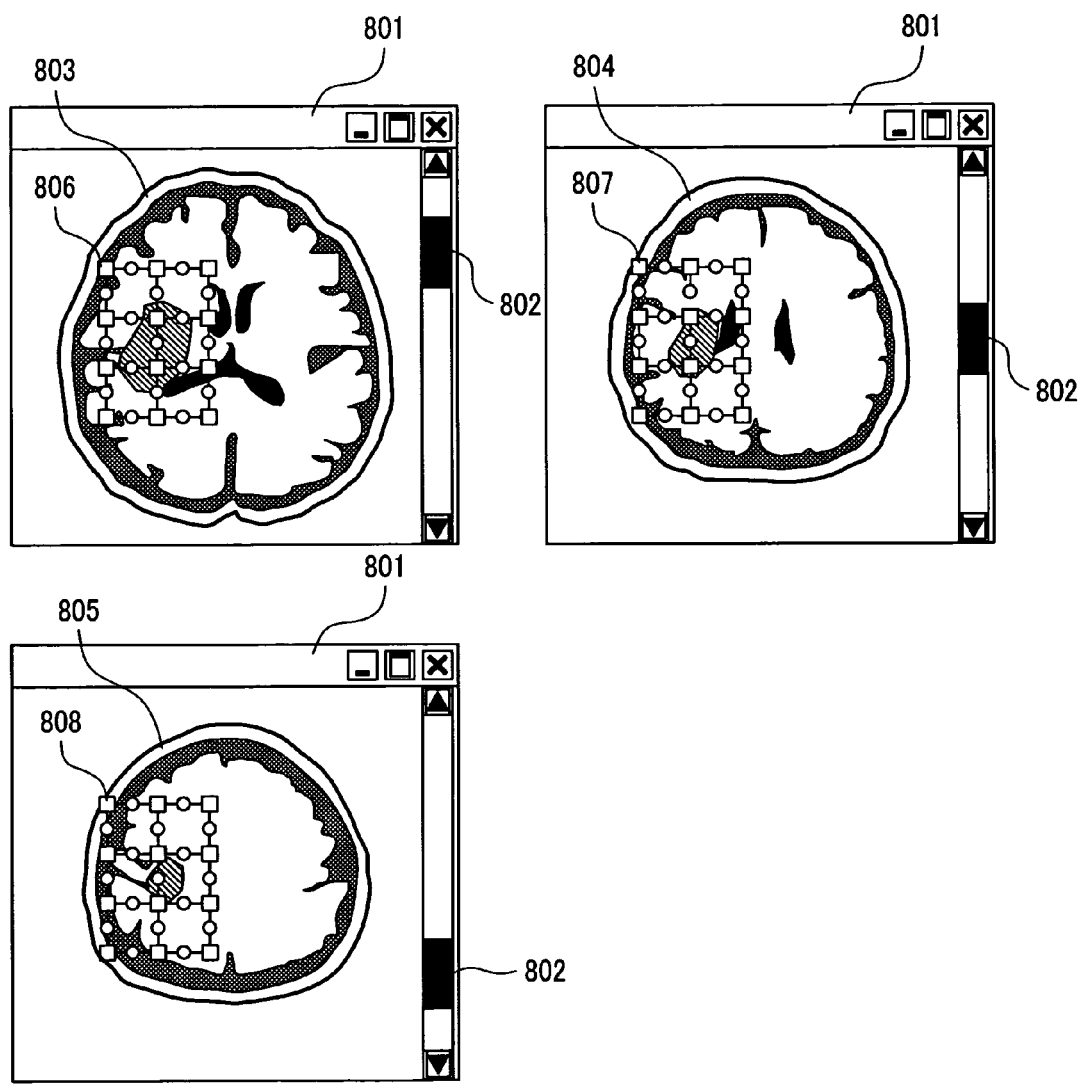
FIG. 8 is an explanatory diagram concerning a method of displaying an anatomical image of a desired section within a window for displaying probe position according to the first or second embodiment.

As far as a three-dimensional anatomical image is concerned, an image of a desired section should preferably be able to be displayed instead of an image of a specific section. In particularly, when a region of interest is determined based on the position of an infarcted area or the like, since a section containing the infarcted area is unknown, a means for retrieving an anatomical image of any section is needed. As shown in FIG. 8, a means to select display section 802 is included in a window for displaying probe position 801 so that anatomical images 803 to 805 expressing desired sections and representations expressing probe positions 806 to 808 projected on the respective sections can be displayed. As for the windows for displaying probe position showing the images of a plurality of sections, different windows may be opened for respective images of sections. Otherwise, a window for displaying probe position may be used in common, and the means to select display section may be used to change representations of probe positions and anatomical images on each of which a representation of a probe position is superimposed.

As shown in FIG. 8, according to the present embodiment, three-dimensional anatomical images of desired sections are displayed. Even when a representation of a probe position may be displayed while being superimposed on a three-dimensional brain functional image constructed using an fMRI system, a PET system, an electroencephalography system, a magnetoencephalography system, an optical bioinstrumentation for living body, or a SPECT system, brain functional images of desired sections are displayed in the same manner.

A representation expressing a lesion such as an infarcted area can be sampled based on a difference in contrast from a representation expressing a peripheral region and being contained in a diffusion-weighted image, a T2-weighted image, or any other kind of MRI image. In this case, a pointing device or the like is used to delineate a region of interest in an anatomical image. Otherwise, the difference in a pixel value from the representation of the peripheral area is utilized in order to automatically or semi-automatically sample a domain containing pixel values, which fall within a specific range, according to a region growing method or the like. If a representation of a lesion is sampled as a representation of a region of interest, images constructed according to various metric methods may have to be observed. For example, a T1-weighted image, a T2-weighted image, a diffusion-weighted image, and a neuronal fiber tracking image that are kinds of MRI images and are by nature different from one another in terms of a contrast between representations of tissues are used to visualize various lesions. Moreover, a combined image constructed by superimposing on an anatomical image a brain functional image constructed by an fMRI system, a PET system, an electroencephalography system, a magnetoencephalography system, an optical bioinstrumentation for living body, or a SPECT system may be employed. Otherwise, the brain functional image alone may be employed.

Figure 10:
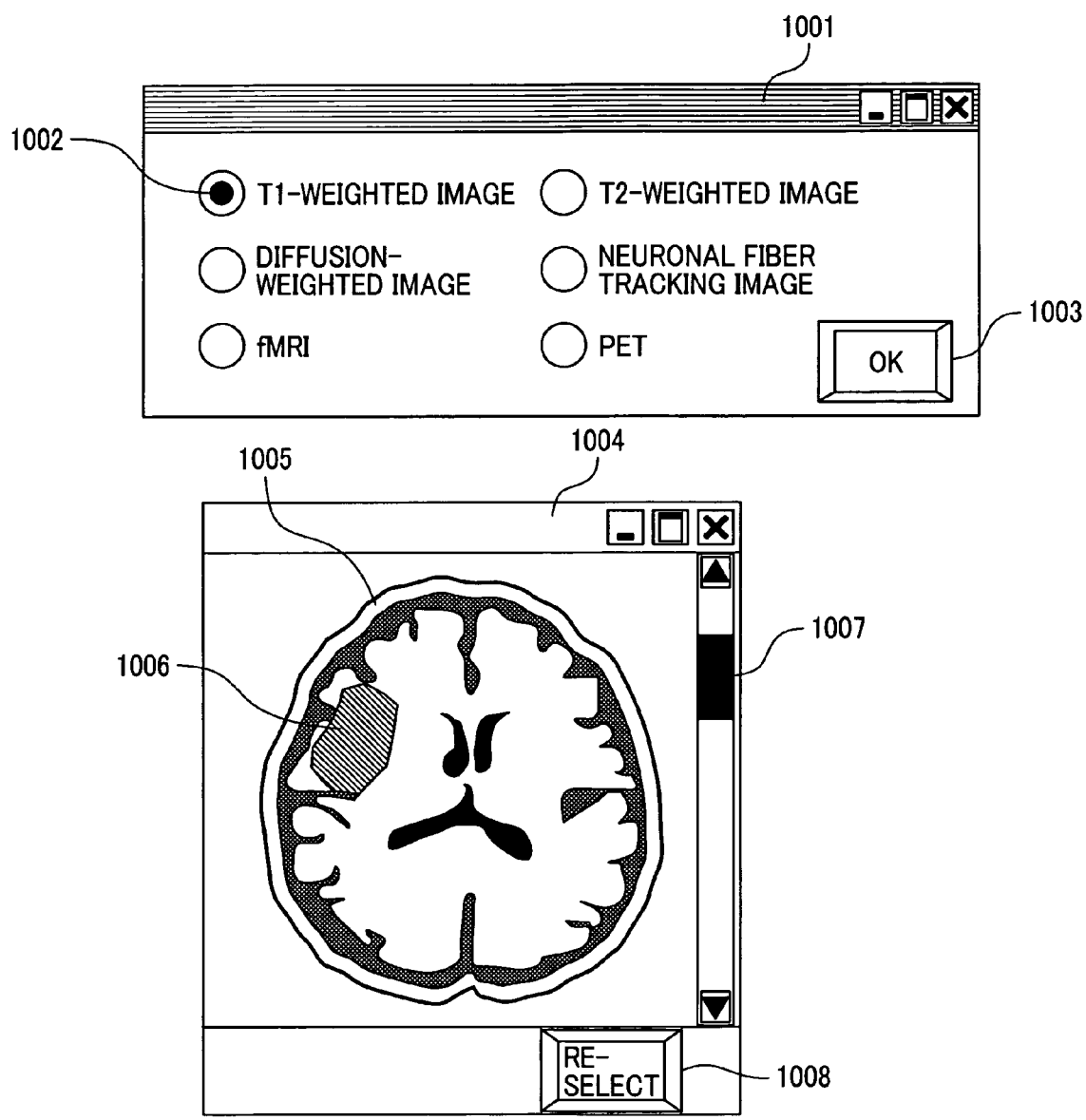
FIG. 10 shows an example of an images electing means included in the first and second embodiments.

Consequently, for example, an image selecting means shown in FIG. 10 should preferably be included. In a select image window 1001, select image buttons 1002 are used to select a kind of image to be displayed. The select image buttons 1002 are, for example, radio buttons. When a mouse is clicked within an OK button 1003, a selected image 1005 is displayed within a region-of-interest/probe position display window 1004. A region of interest 1006 is delineated in an image, and the resultant representation of the region of interest 1006 is superimposed on the selected image. If necessary, a section selecting means 1007 may be used to change images of sections to be displayed. Moreover, if any image other than the selected image must be displayed, the mouse is clicked within a reselection button 1008. A kind of image to be displayed is reselected within the select image window 1001.

If a specific area such as a motor area is regarded as a region of interest, for example, a Brodmann map may be employed. The Brodmann map shows the cerebral cortex that while functionally dividing the cerebral cortex into regions to which numbers are assigned. The relationship of correspondence between the numbers and coordinates representing positions in a standard brain defined by Talairach is already known. Consequently, coefficients of image transformation used to convert the standard brain into an anatomical image are calculated and then used to convert a region, which has a predetermined area number in the Brodmann map, into an image. Thus, a portion of the anatomical image expressing the region of the predetermined numbered area is constructed.

Figure 9:
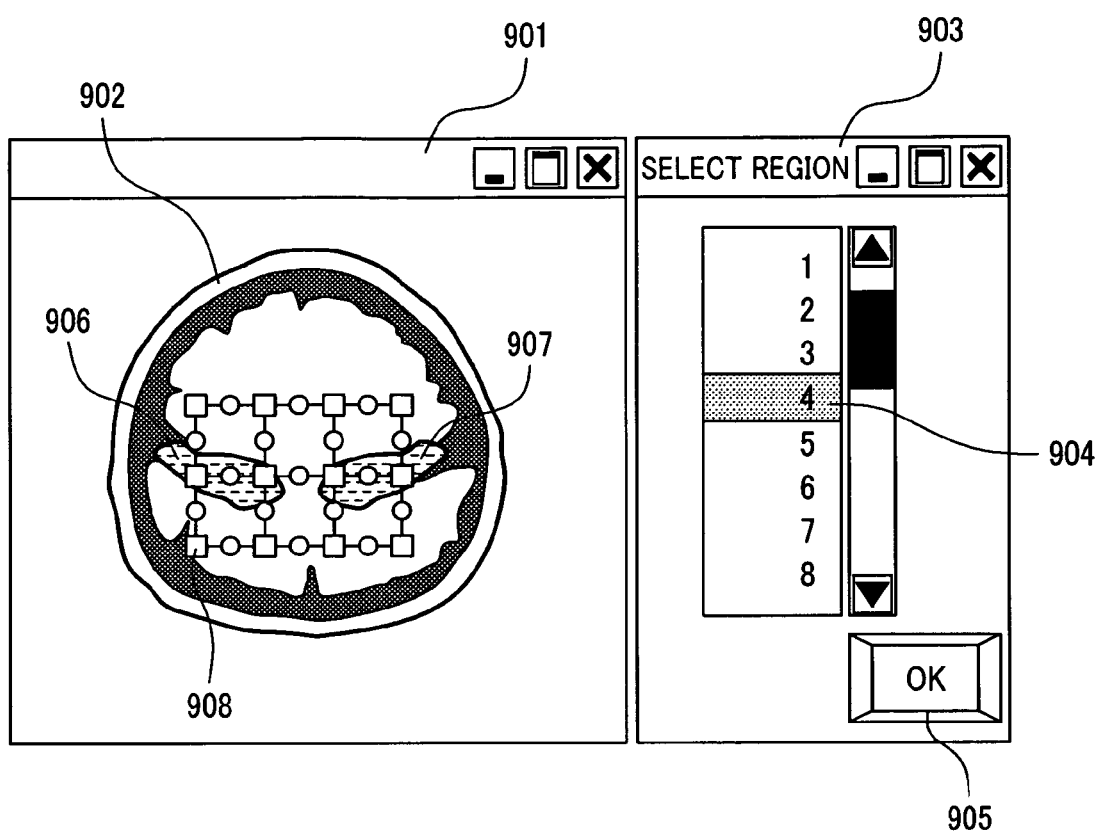
FIG. 9 shows a means for displaying an image by selecting a predetermined numbered area in a Brodmann map according to the first or second embodiment.

FIG. 9 shows a region selecting means and an example of an image displayed in a case where a predetermined numbered area in the Brodmann map is regarded as a region of interest. A representation expressing a region of interest and a representation expressing a probe position are displayed while being superimposed on an anatomical image 902 of any section within a region-of-interest/probe position display window 901. In a region selection window 903, any Brodmann area number 904 is selected and finalized with a click made in a selection button 905. Alternatively, characters indicating an area number may be entered or any other selecting method may be adopted. Assuming that the aforesaid image transformation method is adopted, the region having the selected Brodmann, area number 904 is converted into an image that will fit the anatomical image, and the resultant image is displayed as representations 906 and 907 expressing a region of interest while being superimposed on the anatomical image 902. A recommended probe position 908 is calculated based on the region of interest, and a representation expressing the recommended probe position is superimposed on the anatomical image 902.

Aside from the Brodmann map, for example, an area labeling method based on coordinates representing positions in an MNI standard brain may be adopted (refer to "Neuroimage" written by N. Tzourio-Mazoyer et al. (vol. 15, pp. 273-289, 2002).

Figure 11:
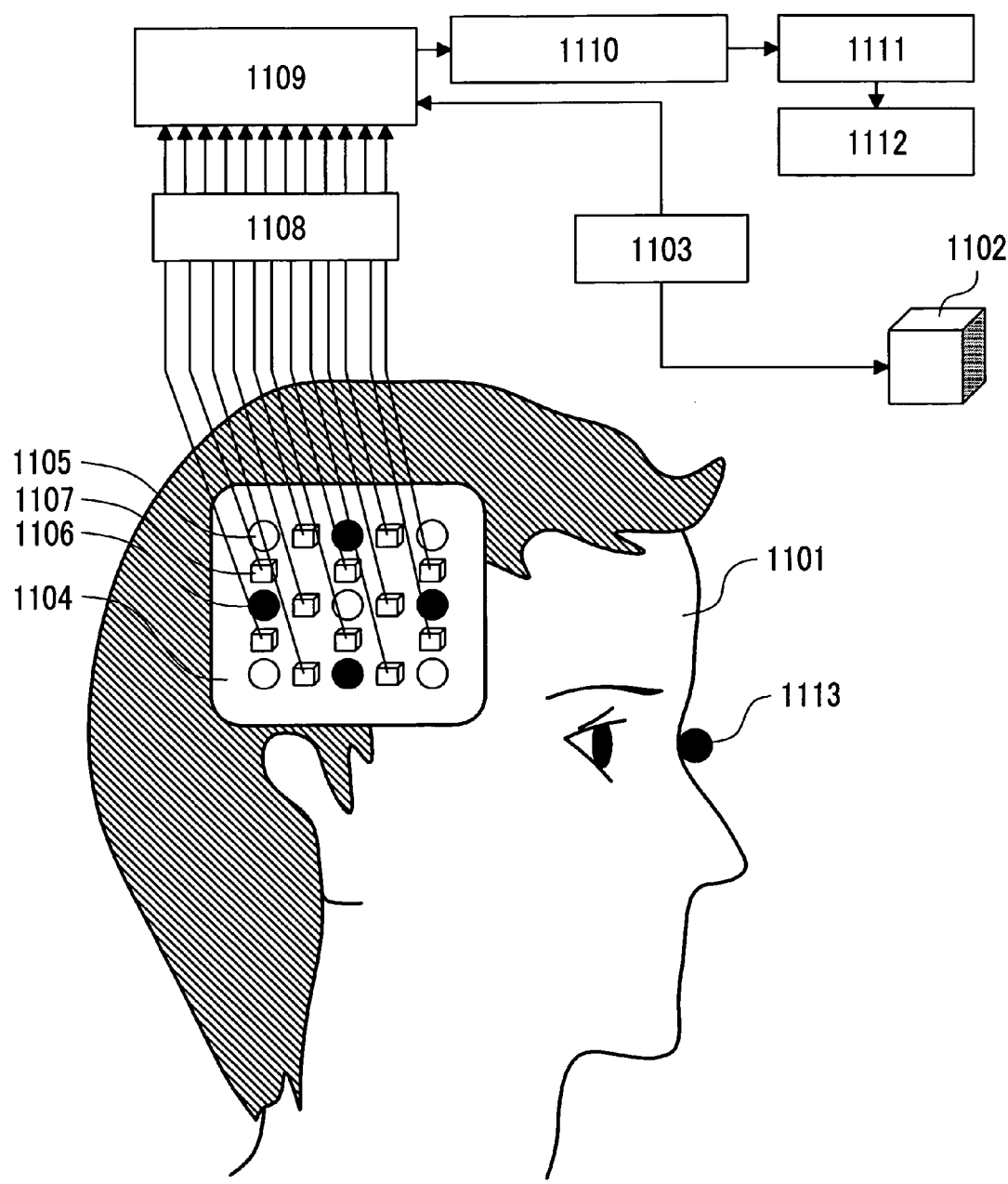
FIG. 11 is an explanatory diagram concerning a position detecting method adopted when a magnetometric sensor type is employed in the first or second embodiment.

A means of detection of probe position includes, for example, a mechanical method, an optical method, a magnetometric sensor method, an acoustic method, and a method using camera scanning. Any of the methods may be adopted. Herein, the magnetometric probe position detecting method will be described in conjunction with FIG. 11.

A magnetic source 1102 includes three coils that induce magnetic fields in three mutually orthogonal directions, and generates a three-dimensional magnetic field along with the flow of an alternating current induced by a drive circuit 1103. A magnetometric sensor 1107 is fixed to a probe 1104 mounted on the head of a subject 1101. The position at which the magnetometric sensor 1107 is fixed is, for example, a substantial midpoint (sampling point) between an irradiation fiber holder 1105 and a detection fiber holder 1106. Preferably, at least three magnetometric sensors are fixed at different positions. The magnetometric sensor 1107 comprises three mutually orthogonal coils and transfers a detection signal to a detector circuit 1108. The detector circuit 1108 amplifies a current that flows through each of the coils when an alternating magnetic field induced by each of the coils included in the magnetic source 102 penetrates through each of the coils of the magnetometric sensor 1107.

Moreover, the magnetometric sensor 1107 is disposed at least one reference point 1113 on the subject 1101. Positional information on the reference point 1113 is transmitted to a unit to compute real space coordinate 1109. The reference point 1113 is a point on scalp defined in a ten/twenty method that is a standard method for disposing electrodes of EEG, for example, a root of nose(nasion), an occipital point (inion), or a right or left preauricular point. For construction of an anatomical image of the subject 1101, a reference point marker is attached to the reference point 1113 in order to calculate coordinates representing the reference point in a coordinate system defined for the anatomical image. For the reference point marker, a material making the reference point marker easily distinguishable in an anatomical image constructed by an imager of anatomical image should preferably be employed. For example, when an MRI system is used to construct an anatomical image, a capsule enclosing vitamin D, vitamin E, or any other fat-soluble chemical substance is regarded as the reference point marker. When X-ray CT is employed, a metallic ball that absorbs X-rays is regarded as the reference point marker.

The unit to compute real space coordinate 1109 regards the position of the magnetic source 1102 as a reference point, and calculates real-space coordinates representing the positions of the magnetometric sensors 1107 attached to the probe 1104 and the reference point 1113 respectively. A unit to compute image space 1110 calculates coordinates representing the reference point 1113 in the coordinate system defined for the anatomical image on the basis of the position of the reference point marker. Furthermore, coordinates representing the position of the probe 1104 in the coordinate system defined for the anatomical image are calculated based on the coordinates representing the reference point 1113 in the coordinate system for the anatomical image, and the real-space coordinates representing the positions of the magnetometric sensors 107. A unit to combine images 1111 constructs a combined image, which has a representation expressing the position of the probe 1104 superimposed on the anatomical image, on the basis of the coordinates representing the position of the probe 1104 in the coordinate system defined for the anatomical image. The combined image is displayed on a display unit 1112.

When a mechanical means of position tracking or a mechanical position sensor is employed, an arm of a manipulator is brought into contact with the reference point 1113 or an arbitrary point on the probe 1104. At this time, a potentiometer or an encoder is used to measure a linear displacement made by the arm and a rotational displacement made thereby. Thus, positional information on the arbitrary point to be discussed in a coordinate system defined for the manipulator is calculated. Positional information on the reference point is detected in the same manner as it is according to a method using magnetometric sensors, whereby relative coordinates are calculated with the coordinates representing the reference point as a reference. Furthermore, positional information on the position of a representation expressing the reference point marker and being contained in the anatomical image is used to calculate coordinates representing the arbitrary position in the coordinate system defined for the anatomical image.

When an optical means of position tracking or an optical position sensor is employed, a marker is attached to the reference point 1113 and an arbitrary position on the probe 1104. Coordinates representing the arbitrary position on the probe 1104 in the coordinate system defined for the anatomical image can be calculated based on images formed using a plurality of CCD cameras, the positions of the CCD cameras, and the positional information on the reference point 1113.

When an acoustic means of position tracking or an acoustic position sensor is employed, the time required for sound waves sent from a wave source to return to a detector after reflecting from an object, and an acoustic velocity are used to calculate the distance between the object and the acoustic position sensor. Otherwise, a phase difference between sound waves sent from the wave source and sound waves returned to the detector after reflecting from the object, and the acoustic velocity are used to calculate the distance between the object and the acoustic means of position tracking or the acoustic position sensor. An arbitrary position on the probe 1104 is selected as the object, and positional information on the arbitrary position to be discussed in a coordinate system defined for the acoustic position sensor is calculated. Moreover, the reference point 1113 is selected as the object, and positional information on the reference point to be discussed in the coordinate system defined for the acoustic position sensor is calculated. Thus, relative coordinates are calculated with the coordinates representing the reference point as a reference. Moreover, coordinates representing the arbitrary position on the probe to be discussed in the coordinate system defined for the anatomical image can be calculated based on the positional information on the position of the reference point marker discussed in the coordinate system defined for the anatomical image.

A camera imaging method is such that a plurality of cameras are used to form images expressing a plurality of angles of a subject on which a probe is mounted. The images expressing the plurality of angles of the subject are used to calculate a three-dimensional outline image of the subject on which the probe is mounted. The three-dimensional image is saved in a memory means. For re-measurement, the probe is remounted on the subject in order to form images expressing a plurality of angles of the subject. An outline image constructed from the images expressing the plurality of angles of the subject and a previous outline image are checked to see if they are consistent with each other. The sequence of changing probe positions, constructing images using the cameras, and verifying whether outline images are consistent with each other is repeated until the consistency between outline images reaches a predetermined degree. An image matching method may be employed in determining the degree of consistency between outline images.

Figure 5:
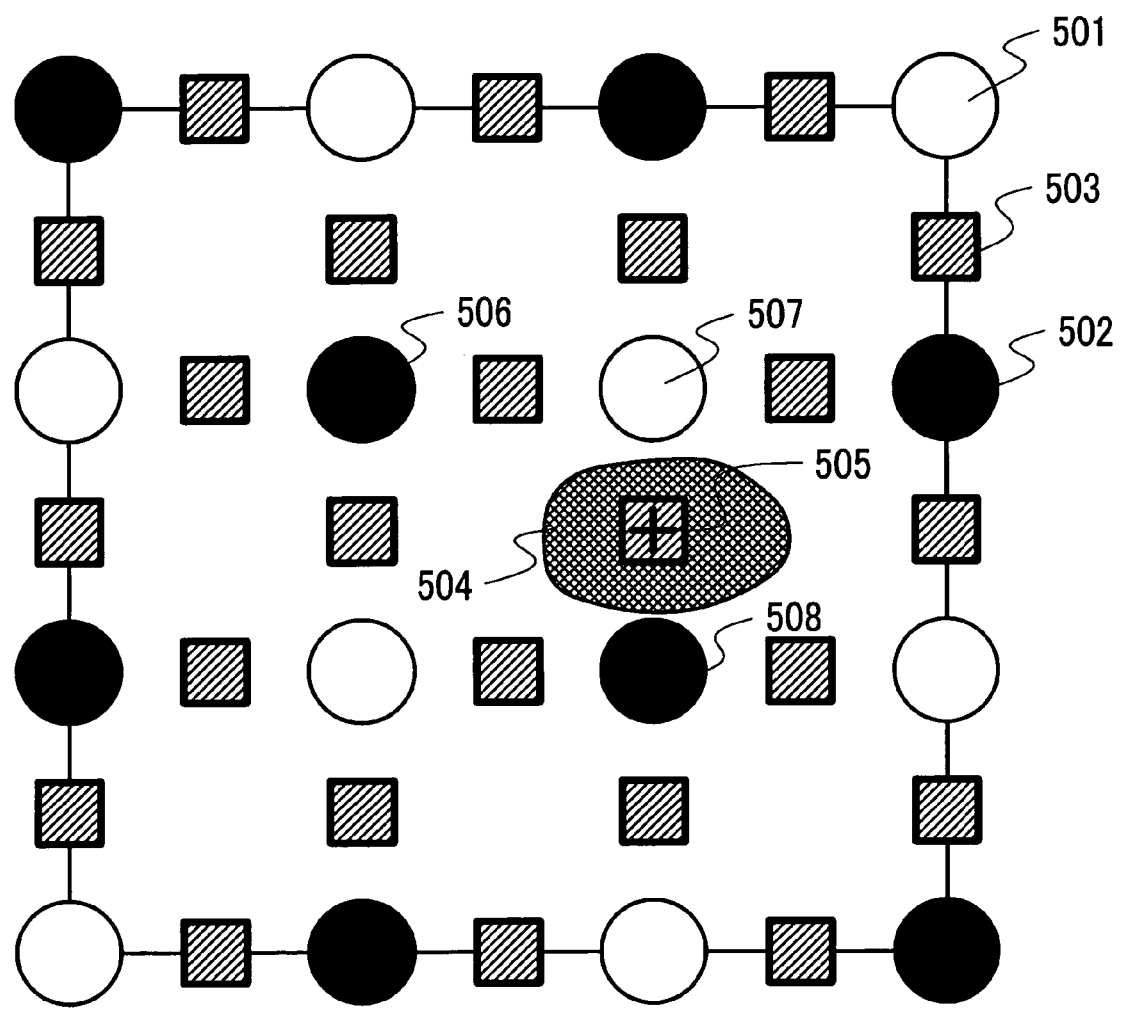
FIG. 5 is an explanatory image concerning a method of determining a recommended probe position according to the first or second embodiment.

Next, a method of determining a recommended probe position will be described in conjunction with FIG. 5. FIG. 5 shows an example of arrangement of holders of incident fiber 501 and holders of detection fiber 502 in a probe included in an optical bioinstrumentation for living body. The holders of incident fiber 501 and holders of detection fiber 502 are equidistantly and alternately arranged. A substantial midpoint between the irradiation fiber holder and the adjoining detection fiber holder is regarded as a sampling point 503. As described previously, the sensitivity in detection of a signal in biomeasurement using light is maximized at the sampling point 503. A recommended probe position is determined so that the center of gravity 505 of a region of interest 504 will be located immediately below the sampling point 503. Since the probe has a plurality of sampling points, a plurality of recommended probe positions are conceivable. In this case, for example, a sampling point located nearest the center of the probe, or in other words, a sampling point whose distance from a current probe position is shortest is selected in order to uniquely determine a recommended probe position.

In calculation of the distance between the recommended probe position and the three-dimensional position of a probe, distances between adjoining ones of at least three points should preferably be taken into consideration. For example, in the example of FIG. 5, points 506, 507, and 508 are predefined as distance calculation points, and distances between a recommended probe position and associated distance calculation points on the probe 307 are calculated. When all the distances between the recommended probe position and the distance calculation points fall within a predetermined range of distances, an alarm device 314 gives the alarm.

Figure 12:
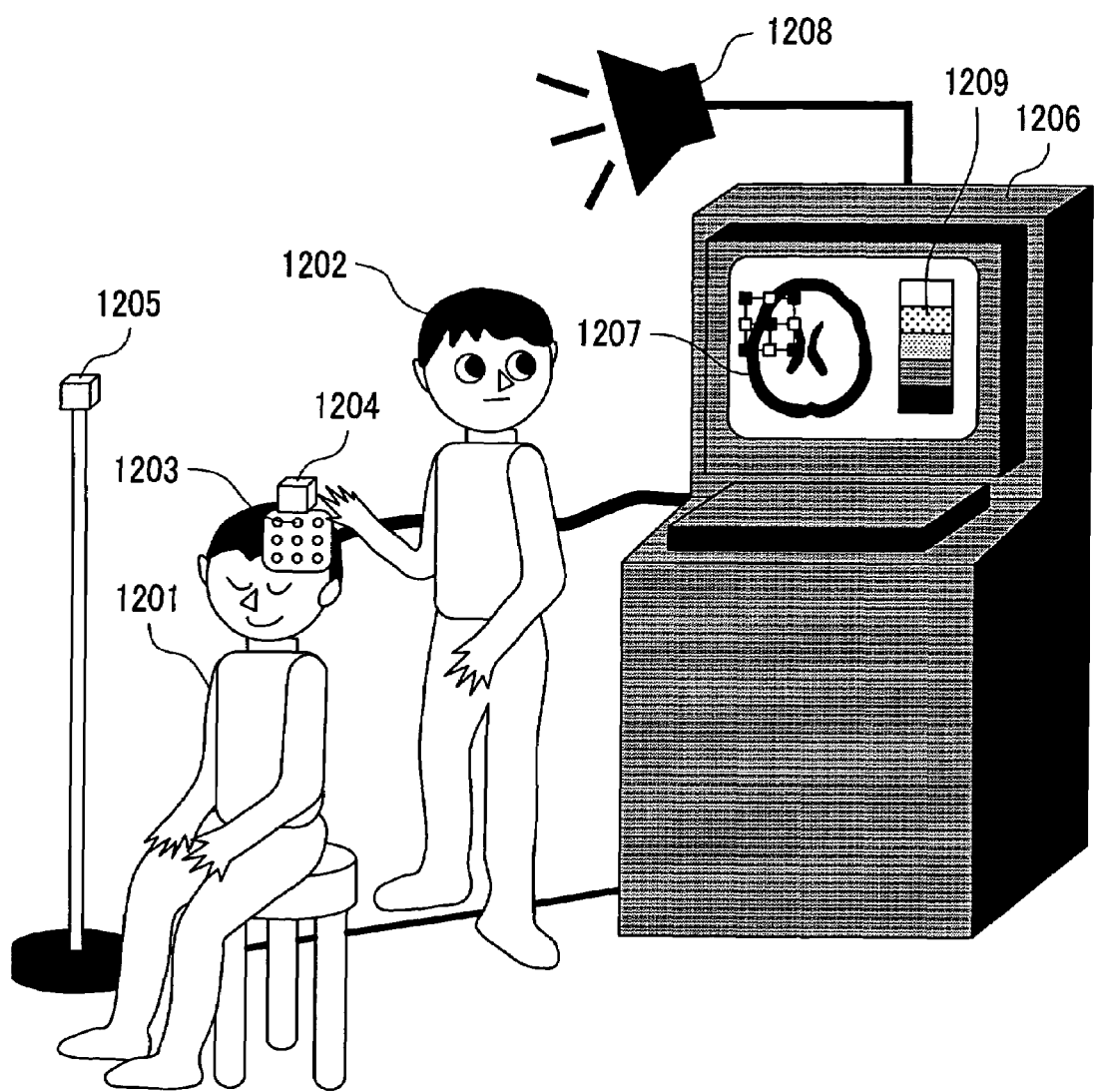
FIG. 12 shows a scene where the optical bioinstrumentation for living body in accordance with the first embodiment is employed.

As shown in FIG. 12, according to the present embodiment, an operator 1202 manually adjusts a probe position. The position of a probe 1203 mounted on the head of a subject 1201 is supported by the operator 1202, and detected by a position sensor composed of a magnetometric sensor 1204 fixed to the probe 1203 and a magnetic source 1205. A representation expressing the detected position of the probe 1203 is displayed within a window for displaying probe position 1207 opened in near-infrared measurement equipment 1206. When the distance between the probe position and a recommended probe position falls within a predetermined range, an alarm device 1208 generates an alarm sound. Otherwise, an indicator 1209 reading a degree of consistency between the probe position and recommended probe position is displayed. Thus, the operator 1202 is notified of the fact that the probe 1203 is located at a desired position. Herein, the position sensor that detects a probe position is of a type employing a magnetometric sensor. However, the present invention is not limited to this type of position sensor.

Next, an example of a previous data referencing means that references a probe position or measurement data, which is employed previously, at the time of re-measurement will be described in conjunction with FIG. 6.

When an input device such as a keyboard or a card reader is used to enter a patient ID, previous data concerning the patient is read from a database. A list of previous data items is displayed in a window of choosing previous data 601. At the same time, the patient ID and a patient name are presented in a field of patient's ID 602 and a field of patient's name 603.

This makes it possible to identify the patient. A field of data number 604, a field of measurement date 605, and a field of remarks 606 are referenced in order to designate previous data 607. In the field of remarks 606, a region to be measured, the contents of a task performed in measurement of brain functions, and other notes concerning conditions for measurement are entered. In the example shown in FIG. 6, a mouse is clicked within the field of data number 604, the field of measurement date 605, or the field of remarks 606 on the line of the desired previous data included in the previous data list. Consequently, the selected line of the previous data is highlighted. In this state, the mouse is clicked within a button for displaying probe position 608 or a button for displaying data 609.

When the mouse is clicked within the button for displaying probe position 608, a probe position at which the selected previous data is acquired is reflected on a window for displaying probe position 610. A representation expressing a probe position 612 at which the previous data is acquired is superimposed on an anatomical image 611. During adjustment of a probe position, a representation expressing a current probe position 613 is also superimposed on the anatomical image. When the mouse is clicked within the button for displaying data 609, a near-infrared optical topographic image 615 of a region specified with the selected previous data is displayed within a window of displaying previous data 614. During adjustment of a probe position, a current probe position 616 is also superimposed on the anatomical image. The button for displaying probe position 608 and the button for displaying data 609 may not be included independently of each other. Alternatively, one button may be used to display a representation expressing a previous probe position and previous data alternately along with a click. Moreover, the window for displaying probe position 610 and the window of displaying previous data 614 may not be included independently of each other. Alternatively, a representation expressing a previous probe position and previous data may be superimposed on the same anatomical image.

Figure 7:
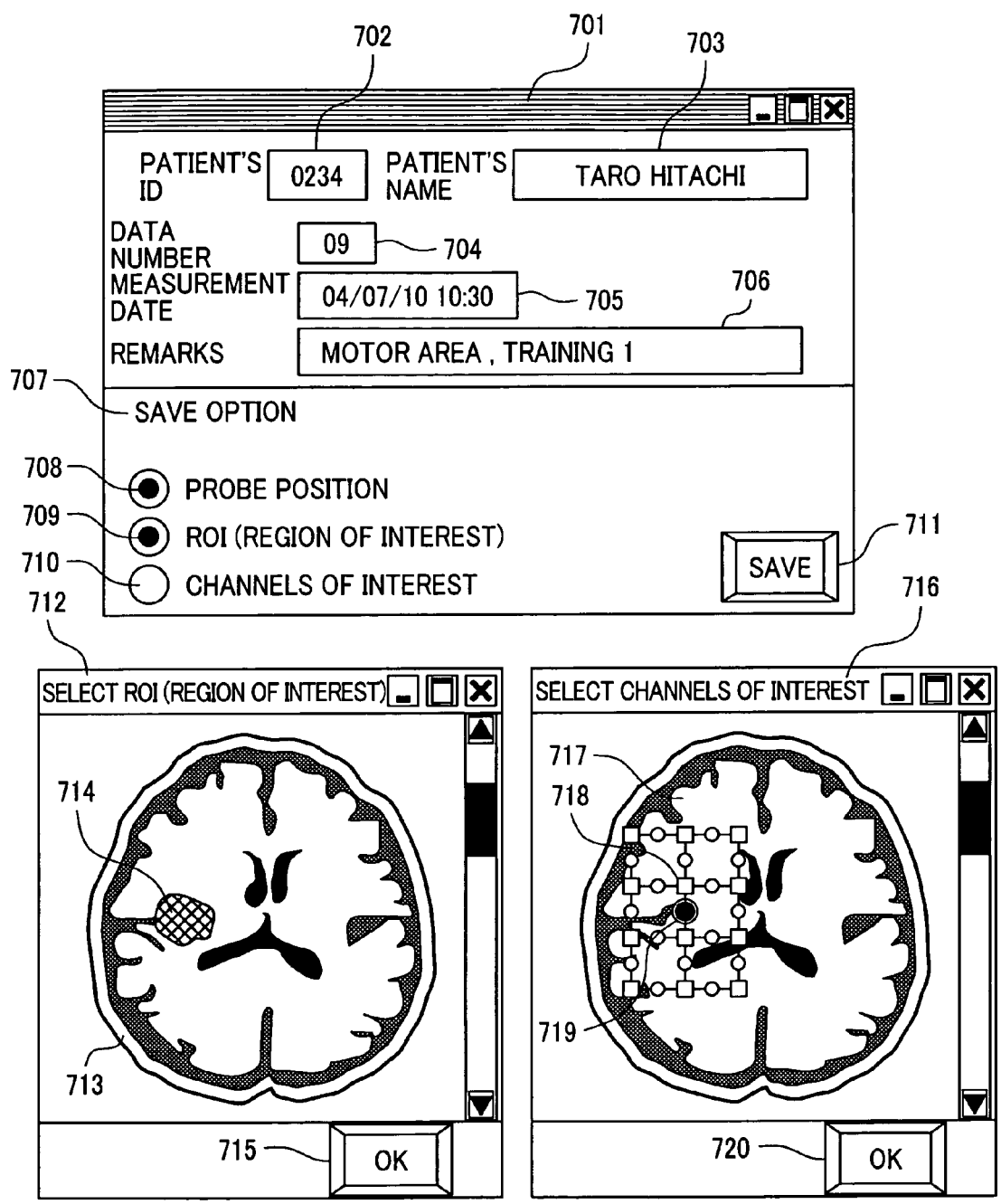
FIG. 7 is an explanatory diagram concerning a method of saving a probe position, a region of interest, and a channel of interest together with data according to the first or second embodiment.

If a probe position, a region of interest, and a channel of interest are saved together with measurement data, it would prove helpful in determining a probe position at the time of re-measurement. Designating an option at the time of saving data will be described in conjunction with FIG. 7.

An input device such as a keyboard or a card reader is used to enter a patient ID and a patient name in a field of patient's ID 702 and a field of patient's name 703 in a window of choosing previous data 701. Furthermore, a data number, a date of measurement, and notes on conditions for measurement are entered in a field of data number 704, a field of measurement date 705, and a field of remarks 706 respectively. Desired optional information such as a probe position 708, a region of interest 709, or a channel of interest 710 is selected in a field to specify save option 707. A mouse is then clicked within a save button 711. Consequently, information on a measured position is saved together with the patient ID, patient name, data number, date of measurement, notes on conditions for measurement, and measurement data.

When the region of interest 709 is selected as an optional item to be saved, a region of interest 714 is delineated in an anatomical image 713 displayed in a window to select ROI 712. The mouse is then clicked within an OK button 715, whereby a representation expressing the region of interest to be saved is determined. The region of interest may be delineated using the pointing device as described above. Alternatively, a region growing method or the like may be adopted in order to segment a domain having pixel values that fall within a specific range. Otherwise, a Brodmann map or the like may be used to designate a specific region. If the channel of interest 719 is selected as an optional item to be saved, the channel of interest 719 is designated on a representation expressing a probe position 718 in an anatomical image 717. The mouse is then clicked within the OK button 720, whereby a channel of interest to be saved is determined. A plurality of channels of interest 719 may be selected.

Referring to FIG. 1 to FIG. 3, a procedure for implementing the present invention will be described below.

First, if construction of an anatomical image is needed (step 101), an anatomical image of a subject 301 is constructed (step 102). The anatomical image is saved in a memory unit 303 (step 103). If a previously constructed anatomical image is employed, actions of steps 102 and 103 are not carried out. Prior to measurement to be performed using an optical bioinstrumentation for living body, a probe position is determined. A desired anatomical image is selected from among data items saved in the memory unit 303 (step 104), and then displayed on a display unit 304 (step 105). At this time, if previous data is available (step 106), a representation expressing a probe position at which the previous data is acquired may be superimposed on the anatomical image (step 107). Referring to the anatomical image and previous probe position, a selecting region unit 305 is used to delineate a region of interest (step 108). A computing unit 306 calculates a recommended probe position on the basis of the region of interest (step 109).

Thereafter, the computing unit 306 calculates a distance R between a current probe position detected by a probe position sensor 308 and the recommended probe position (step 110). If the distance R gets smaller than a predefined threshold Rt (step 111), an acoustic or visual alarm is generated (step 112). Thereafter, an amount of light received is measured (step 113). The position of a probe is checked to see if the probe is located at a position at which sufficient measurement sensitivity is ensured. If the probe position must be readjusted because of insufficient sensitivity (step 114.), the probe position is changed from one position to another. The actions of steps 110 to 113 are repeated until sufficient measurement sensitivity is ensured. After the probe position is determined, a biomedical optical signal is measured (step 115). Data and the probe position are saved in the memory unit 303 (step 116).

Figure 14:
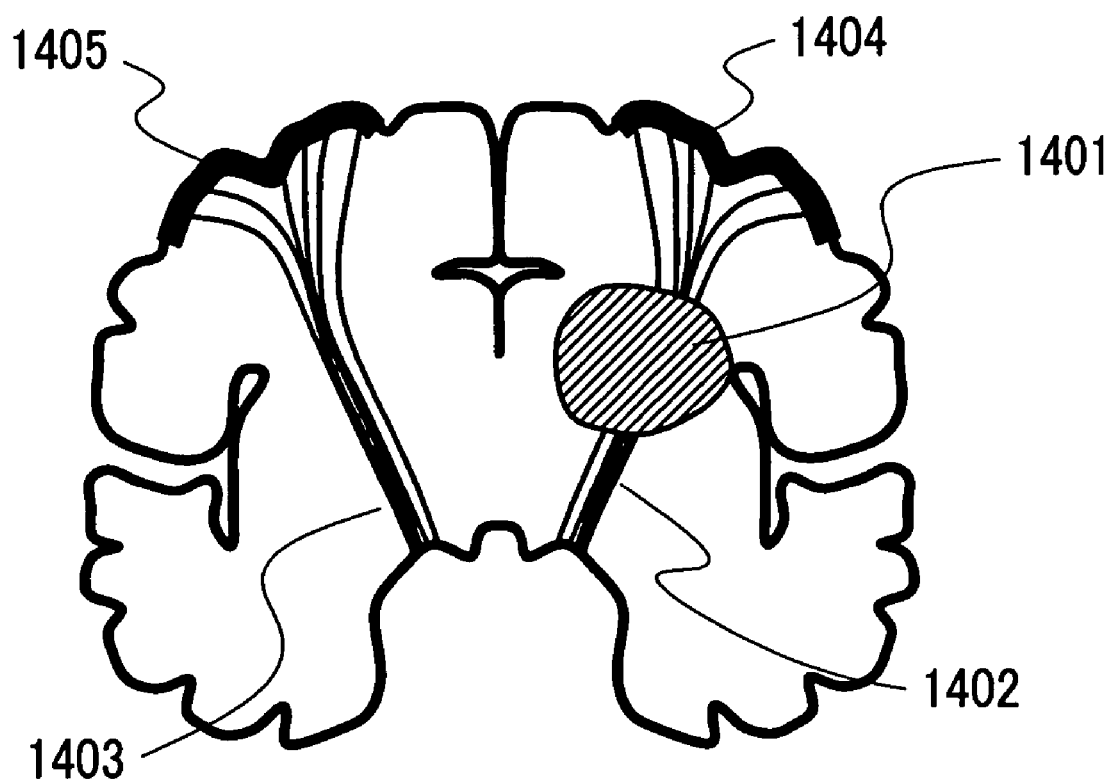
FIG. 14 shows a case where an infarcted area is present in a deep region in the brain.

As described previously, an optical bioinstrumentation for living body is equipment for measuring a change in the concentration of hemoglobin in the cerebral cortex, and is unsuitable for measurement of a deep cerebral region. On the other hand, cerebral infarction occurs not only in a region near the cerebral cortex but also in a deep region. However, even if an infarcted area exist in the deep cerebral region, observation of an anatomical image containing information on the infarcted area has a significant meaning in determining a probe position for biomeasurement using light. For example, as shown in FIG. 14, if an infarcted area 1401 exists in the middle of the right pyramidal tract 1402, a neural circuit in the motor system becomes defective. This will cause the activity of the right motor area 1404 located at the terminal of the right pyramidal tract 1402 to change. Otherwise, the activity of the left motor area 1405 located at the terminal of the left pyramidal tract 1403 substantially symmetrically to the right motor area should be observed.

Second Embodiment

Figure 13:
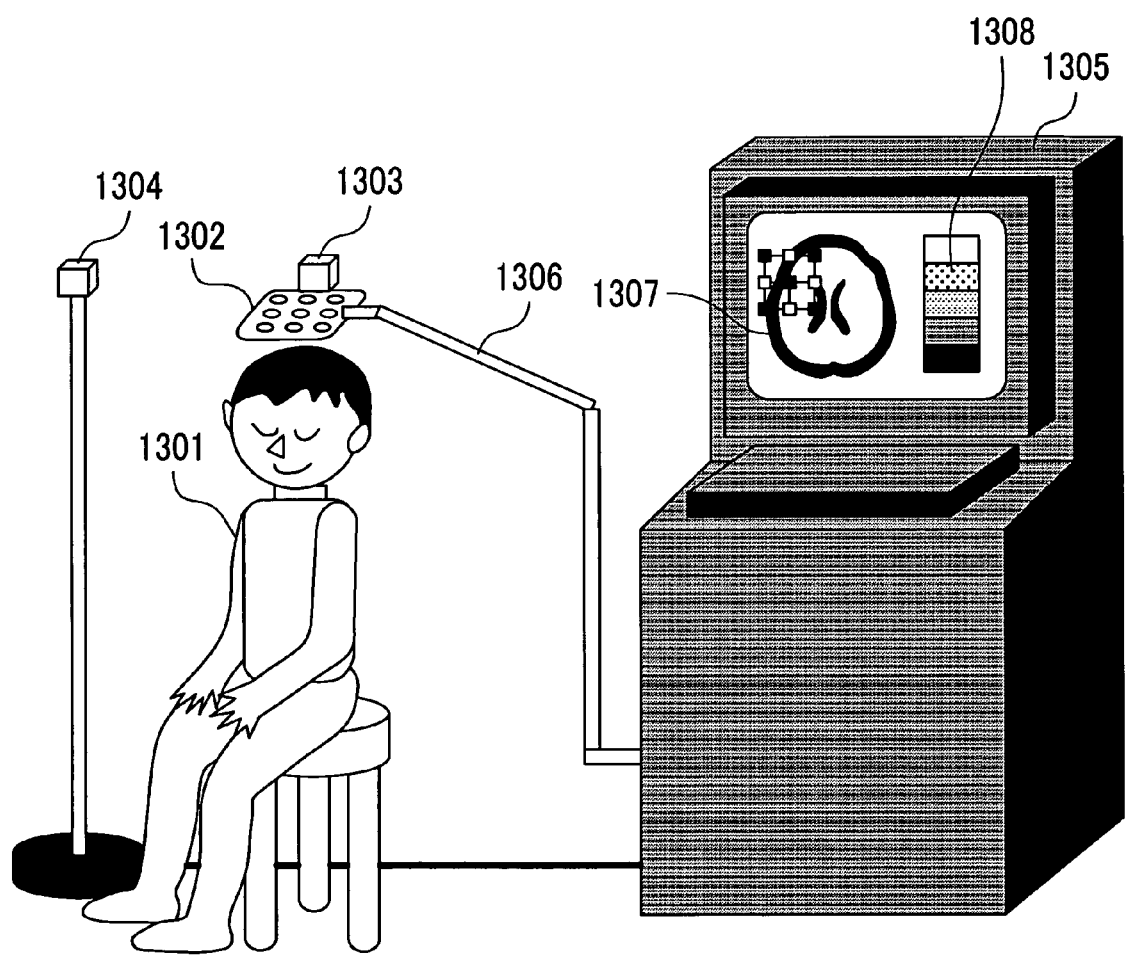
FIG. 13 shows a scene where the optical bioinstrumentation for living body in accordance with the second embodiment is employed.

The second embodiment is almost identical to the first embodiment. Only a prominent point will be described in conjunction with FIG. 14 and FIG. 13.

Figure 4:
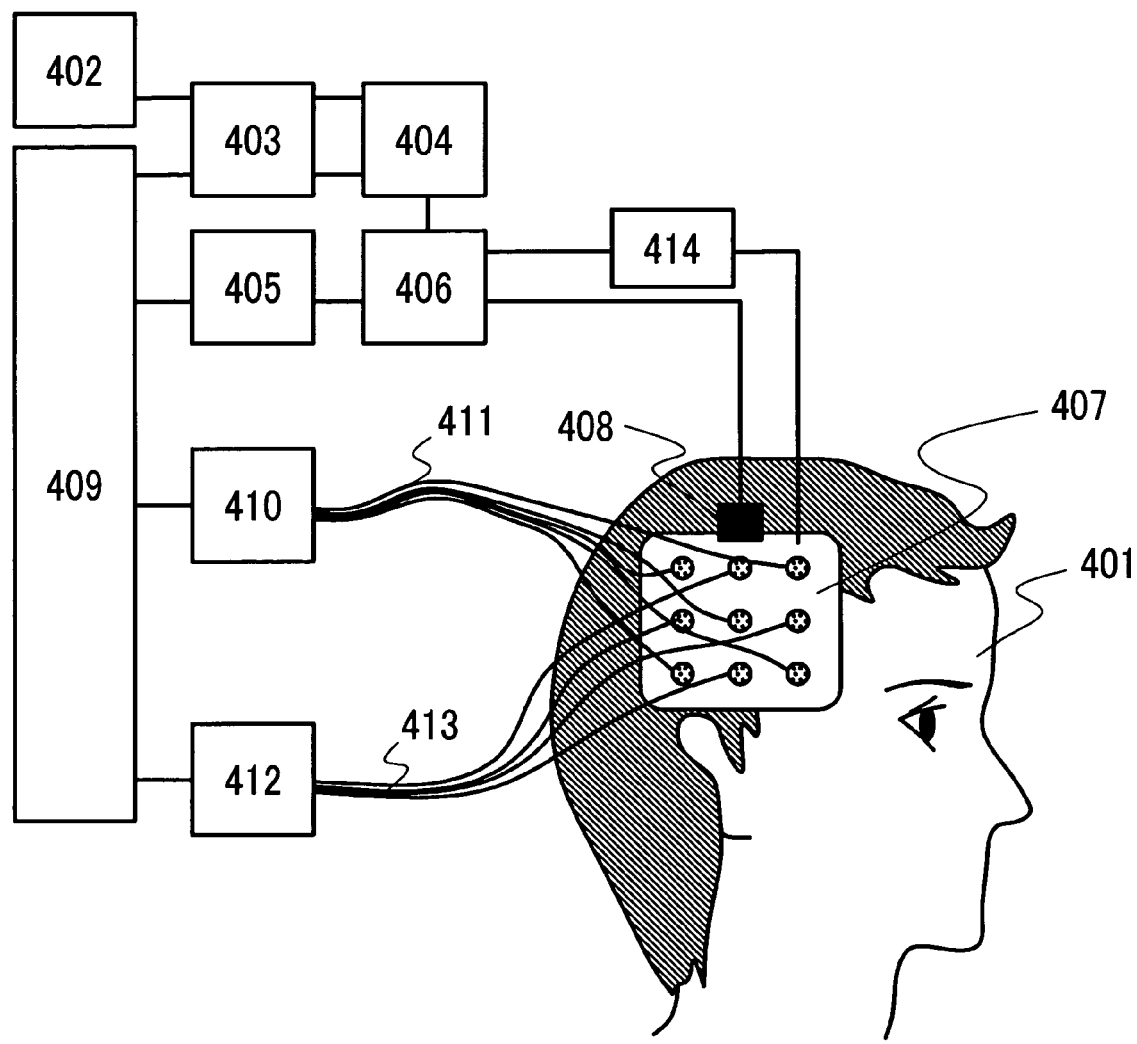
FIG. 4 is an explanatory image showing the configuration of the second embodiment.

Another configuration of an optical bioinstrumentation for living body in accordance with the present invention will be described in conjunction with FIG. 4. An anatomical image of a subject 401 constructed in advance using an imager of anatomical image 402 is saved in a memory unit 403. An optical measurement and control unit 409 reads the anatomical image from the memory unit 403 and displays it on a display unit 404. A regions electing unit 405 is used to delineate a region of interest. A computing unit 406 calculates a recommended probe position according to the region of interest.

An optical fiber 411 is coupled to a probe 407 mounted on the head of the subject 401. Light irradiated from an optical irradiator 410 in response to an instruction issued from the optical measurement and control unit 409 is applied to the scalp of the subject 401 after traveling along the optical fiber 411. The light passing through the scalp of the subject 401 travels along an optical fiber 413 coupled to the probe 407, and is then detected by an optical detector 412. A computing unit 406 performs signal processing. A probe position sensor 408 fixed to the probe 407 detects a three-dimensional position of the probe 407.

The computing unit 406 constructs a combined image by superimposing on the anatomical image, which is saved in the memory unit 403, a representation expressing the recommended probe position and a representation expressing the three-dimensional position of the probe 407. The combined image is then displayed on the display unit 404. The computing unit 406 calculates the distance between the recommended probe position and the three-dimensional position of the probe 407. A probe position control unit 414 disposes the probe 407 at the recommended probe position according to the distance.

According to the present embodiment, a probe 1302 is fixed to a distal end of a probe position control arm 1306, and moved on the surface of the head of a subject 1301. The movement of the probe position control arm 1306 is controlled by a control unit incorporated in near-infrared measurement equipment 1305. A position sensor composed of a magnetometric sensor 1303 fixed to the probe 1302 and a magnetic source 1304 detects the position of the probe 1302. A representation expressing the position of the probe 1302 is displayed within a window for displaying probe position 1307 in the near-infrared measurement equipment 1305. When the distance between the probe position and a recommended probe position falls within a predetermined range, the movement of the probe position control arm 1306 is ceased. The position of the probe 1302 is finalized. An indicator 1308 that reads a degree of consistency of the probe position with the recommended probe position may be used to indicate the degree of consistency of the probe position with the recommended probe position. Herein, the position sensor that detects a probe position is of the type employing a magnetometric sensor. The present invention is not limited to this type of position sensor.

As described so far, according to the present invention, there is provided an optical bioinstrumentation for living body in which an optical irradiator and an optical detector are located at a position at which sensitivity is maximized and which exhibits high positional reproducibility at the time of remounting a probe.

What is claimed is:

1. An optical bioinstrumentation for living body comprising:
   a probe that includes an irradiator which irradiates light to a subject and a detector which detects transilluminated light having been irradiated from the irradiator and having been propagated through the subject, and that is mountable on the subject;
   a computing unit that calculates a concentration of metabolite in the subject according to a signal detected by the detector;
   a position sensor that detects a three-dimensional position of the probe; and
   a display unit that displays an indicator indicating the concentration of metabolite calculated by the computing unit; wherein:
   the computing unit is further configured to determine a position on the subject at which the probe should be disposed where the positions on the subject of the irradiator and the detector are positions at which normals to the positions on the subject of the irradiator and the detector intersect an area of interest of an anatomical image of the subject or a brain functional image thereof,
   further wherein the display unit displays representations expressing the determined positions on the subject of the irradiator and the detector superimposed on the anatomical image of the subject or the brain functional image.

2. The optical bioinstrumentation for living body according to claim 1, wherein:
   a substantial midpoint between the irradiator and the detector is regarded as a sampling point; and
   representations expressing the positions on the subject of the irradiator and the detector and a representation expressing the position of the sampling point are displayed on the display unit while being superimposed on the anatomical image of the subject or the brain functional image thereof.

3. The optical bioinstrumentation for living body according to claim 1, further comprising a memory unit in which the anatomical image of the subject or the brain functional image thereof is saved, wherein:
   representations expressing the positions on the subject of the irradiator and the detector are displayed on the display unit while being superimposed on the anatomical image or brain functional image saved in the memory unit.

4. The optical bioinstrumentation for living body according to claim 1, further comprising an alarm device that gives an alarm when the distance between a predetermined region to be measured, which is expressed by a representation contained in the anatomical image or brain functional image, and the position of the sampling point falls within a predetermined range.

5. The optical bioinstrumentation for living body according to claim 4, wherein alarm device is realized with an audio apparatus or a representation signifying that the alarm is given is displayed on the display unit.

6. The optical bioinstrumentation for living body according to claim 1, wherein when a distance between a predetermined region to be measured, which is expressed by a representation contained in the anatomical image or brain functional image, and the three-dimensional position of the probe falls within a predetermined range, the alarm is given.

7. The optical bioinstrumentation for living body according to claim 4, further comprising a control unit that uses the position sensor to dispose the probe at the position on the subject corresponding to the predetermined region to be measured that is expressed by a representation contained in the anatomical image or brain functional image.

8. The optical bioinstrumentation for living body according to claim 1, wherein the anatomical image or brain functional image is a three-dimensional image.

9. The optical bioinstrumentation for living body according to claim 1, wherein the anatomical image is an MRI image of the subject or an X-ray CT image thereof, the brain functional image is any of an fMRI image of the subject, a PET image thereof, an electroencephalogram thereof, a magnetoencephalogram thereof, an optical image for living body thereof, and a SPECT image thereof.

10. An optical bioinstrumentation for living body comprising:
   a probe that includes an irradiator which irradiates light to a subject and a detector which detects transilluminated light having been irradiated from the irradiator and having been propagated through the subject, and that is mountable on the subject;
   a computing unit that calculates a concentration of metabolite in the subject according to a signal detected by the detector;
   a position sensor that detects a three-dimensional position of the probe; and
   a display unit that displays an indicator indicating the concentration of metabolite calculated by the computing unit; and
   a memory unit in which measurement data is saved, wherein:
   the computing unit is further configured to determine a position on the subject at which the probe should be disposed where the positions on the subject of the irradiator and the detector are positions at which normals to the positions on the subject of the irradiator and the detector intersect an area of interest of an anatomical image of the subject or a brain functional image thereof,
   further wherein the display unit displays representations expressing the determined positions on the subject of the irradiator and the detector superimposed on the anatomical image of the subject or the brain functional image.

11. The optical bioinstrumentation for living body according to claim 10, wherein:
   representations expressing the positions on the subject of the irradiator and the detector, and representations expressing positions on the subject at which the irradiator and the detector are disposed at the time of previous measurement are displayed on the display unit while being superimposed on the anatomical image of the subject or the brain functional image thereof; and
   a position on the subject at which the probe should be disposed for re-measurement is determined.

12. The optical bioinstrumentation for living body according to claim 10, wherein a substantial midpoint between the irradiator and the detector is regarded as a sampling point, and representations expressing the positions on the subject of the irradiator and the detector and a representation expressing the position of the sampling point are displayed while being superimposed on the anatomical image of the subject or the brain functional image thereof.

13. The optical bioinstrumentation for living body according to claim 10, further comprising an alarm device that gives an alarm when the distance between a predetermined region to be measured expressed by a representation contained in the anatomical image or brain functional image and the sampling point falls within a predetermined range.

14. The optical bioinstrumentation for living body according to claim 10, further comprising an alarm device that gives an alarm when positions on the subject at which the irradiator and the detector are disposed at the time of previous measurement, and the current positions of the irradiator and the detector fall within a predetermined range.

15. The optical bioinstrumentation for living body according to claim 13, wherein the alarm device is an audio apparatus that generates an alarm sound, or a representation signifying that the alarm is given is displayed on the display unit.

16. The optical bioinstrumentation for living body according to claim 10, wherein the anatomical image or brain functional image is a three-dimensional image.

17. The optical bioinstrumentation for living body according to claim 10, wherein the anatomical image is an MRI image of the subject or an X-ray CT image thereof, and the brain functional image is any of an fMRI image of the subject, a PET image thereof, an electroencephalogram thereof, a magnetoencephalogram thereof, an optical image for living body thereof, and a SPECT image thereof.

18. An optical bioinstrumentation for living body comprising:
   a probe that includes a plurality of irradiators which irradiate light to a subject and a plurality of detectors which detect transilluminated light having been irradiated from the irradiators and having been propagated through the subject, and that is mountable on the subject;
   a computing unit that calculates a concentration of metabolite in the subject according to a signal detected by the detectors;
   a display unit that displays an indicator indicating the concentration of metabolite calculated by the computing unit; and
   a memory unit in which measurement data is saved, wherein:
   a substantial midpoint between the irradiators and the detectors is regarded as a sampling point;
   representations expressing the positions on the subject of the irradiators and the detectors and representations expressing positions on the subject at which the irradiators and the detectors are disposed at the time of previous measurement are displayed on the display unit while being superimposed on the anatomical image of the subject or a brain functional image thereof;
   when the distance between a predetermined region to be measured, which is expressed by a representation contained in the anatomical image or the brain functional image, and the position of the sampling point falls within a predetermined range, or when positions on the subject at which the irradiators and the detectors are disposed at the time of previous measurement and the current positions of the irradiators and the detectors fall within a predetermined range, an alarm is given; and
   the positions on the subject of the irradiators and the detectors superimposed on an anatomical image of the subject or the brain functional image thereof, are positions at which normals to the positions on the subject of the irradiators and the detectors intersect a section of the anatomical image of the subject or the brain functional image thereof which includes an area of interest internal to the subject.

* * * * *